(12) United States Patent
Brumm

(10) Patent No.: US 8,088,612 B2
(45) Date of Patent: Jan. 3, 2012

(54) THERMOSTABLE CELLULASE AND METHODS OF USE

(75) Inventor: Phillip J. Brumm, Fitchburg, WI (US)

(73) Assignee: C5-6 Technologies, Inc., Middleton, WI (US)

( * ) Notice: Subject to any disclaimer, the term of this patent is extended or adjusted under 35 U.S.C. 154(b) by 141 days.

(21) Appl. No.: 12/604,985

(22) Filed: Oct. 23, 2009

(65) Prior Publication Data

US 2010/0107282 A1    Apr. 29, 2010

Related U.S. Application Data

(60) Provisional application No. 61/108,216, filed on Oct. 24, 2008.

(51) Int. Cl.
| | |
|---|---|
| C12N 9/42 | (2006.01) |
| C12N 9/14 | (2006.01) |
| C12N 9/24 | (2006.01) |
| C12N 15/82 | (2006.01) |
| C12N 15/09 | (2006.01) |

(52) U.S. Cl. ............... 435/209; 435/69.1; 435/320.1; 435/468; 424/94.61; 800/278; 800/284; 536/23.6; 536/23.2

(58) Field of Classification Search .............. None
See application file for complete search history.

(56) References Cited

U.S. PATENT DOCUMENTS

| | | | |
|---|---|---|---|
| 6,680,426 | B2 | 1/2004 | Daniell et al. |
| 7,033,627 | B2 | 4/2006 | Van Ooyen et al. |
| 2007/0256197 | A1 | 11/2007 | Brumm |
| 2008/0233175 | A1 | 9/2008 | Steer et al. |

OTHER PUBLICATIONS

Lucas et al., "Glycoside hydrolase family 5," NCBI, retrieved Dec. 12, 2009, 2 pages, submitted 2008.
Dodson et al., "Endoglucanase H," NCBI, retrieved Dec. 12, 2009, 2 pages, submitted 2008.
Lee et al., "Characterization of the Active Site and Thermostability Regions of Endoxylanase from *Thermoanaerobacterium saccharolyticum* B6A-RI," J. Bacteriol, 1993, pp. 5890-5898, vol. 175(18), American Society for Microbiology.
Hespell et al., "Hydrolysis by Commercial Enzyme Mixtures of AFEX-Treated Corn Fiber and Isolated Xylans," Appl. Biochem. Biotech, 1997, pp. 87-97, vol. 62, Human Press Inc.

*Primary Examiner* — Brent T Page
(74) *Attorney, Agent, or Firm* — Joseph T. Leone, Esq.; Daniel A. Blasiole; DeWitt & Ross & Stevens, S.C.

(57) ABSTRACT

A *Dictyoglomus turgidum* thermostable cellulase enzyme with both endocellulase activity and exocellulase activity that is able to degrade cellulose in the absence of scaffoldins and other cellulosomic proteins is provided. The use of the enzyme to degrade cellulosic materials to soluble sugars is also provided. Also described are nucleic acid constructs that encode and express the cellulase, and hosts transformed to contain the nucleic acid constructs.

31 Claims, 3 Drawing Sheets

FIG. 1

```
DtuC2  ----------------MN---------NLPIKRGINFGDALEAPYEGAWSGYIIKDEYFKI   36
Tsp    MKNFLLFLLMILIMGGIVMGVDPFERNKILGRGINIGNALEAPNEGDWG-VVIKDEFFDI   59
                         *   . :  .**:**:.** :****.*:**  .*****:*:*

DtuC2  VKDAGFDHVRIPIKWSVYTQKEAPYSIEKRIFDRVDHLIEEGLKNNLHVIINIHHYEEIM   96
Tsp    IKEAGFSHVRIPIRWSTHAYAFPPYKIMDRFFKRVDEVINGALKRGLAVVINIHHYEELM  119
       :*:***.******:**  : :.  **.::**..***::*: **:.* *:********:*

DtuC2  EDPLGEKERFLAIWRQISEHYKDYPNNLYFELLNEPTQNLSSELWNQFLKEAIEVIRRTN  156
Tsp    NDPEEHKERFLALWKQIADRYKDYPETLFEILNEPHGNLTPEKWNELLEEALKVIRSID  179
        **  :******:*:**::.******:.*** *****  **. * ** :*:**:***  :

DtuC2  PERKIIVGPDNWNSLYNLEKLIIPENDENIITFHYYNPEFHQGAGWVK-IDLPVGVK     215
Tsp    KNHTIIGTAEWGGISALEKLSVPEWEKNSIVTIHYNPFEFTHQGAEWVEGSEKWLGRK   239
         ::**  :::* .:. ****:*** :: :: :*** ** ****.** . : :  *

DtuC2  WLGTEEKREIERELDMAVSWAEEHGNIPLYMGEFGAYSKADMESRVRWTDEVARSAEKR  275
Tsp    WGSPDDQKHLIE-EFNFIEEWSKKN-KRPIYIGEFGAYRKADLESRIKWTSFVVREMEKR  297
       *  .::::::*  * ::.*.:::  : **:::*****.:***:***::**: *.:*:**

DtuC2  GIAWSYWEFYSGFGVFDPEKNEWRTPLLRALIPERNI-       312  (SEQ. ID. NO: 2)
Tsp    RWSWAYWEFCSGFGVYDTLRKTWNKDLLEALIGGDSIE       335  (SEQ. ID. NO: 4)
        .:*:**** .****.*   :..::  **.***   .:
```

Legend

A: Promega-brand Broad Range Molecular Weight Markers
B: *E. coli* lysate, 1x
C: *E. coli* lysate, 3x
D: Heat-treated lysate, 1x
E: Heat-treated lysate, 3x
F: Concentrated Q Sepharose active fractions, 1x
G: Concentrated Q Sepharose active fractions, 3x
H: Concentrated S-100 active fractions, 1x
I: Concentrated S-100 active fractions, 3x
J: Concentrated S-100 active fractions, 5x

SEQUENCE LISTING

```
<160> NUMBER OF SEQ ID NOS: 7

<210> SEQ ID NO 1
<211> LENGTH: 939
<212> TYPE: DNA
<213> ORGANISM: Dictyoglomus turgidum
<220> FEATURE:
<221> NAME/KEY: CDS
<222> LOCATION: (1)..(939)

<400> SEQUENCE: 1 atg aac aat ctt cct att aag aga gga att aat ttt ggg gat gct tta      48
Met Asn Asn Leu Pro Ile Lys Arg Gly Ile Asn Phe Gly Asp Ala Leu
1               5                   10                  15 gaa gct cct tat gag ggg gct tgg agt ggt tat ata att aag gat gaa      96
Glu Ala Pro Tyr Glu Gly Ala Trp Ser Gly Tyr Ile Ile Lys Asp Glu
            20                  25                  30 tat ttt aaa att gtt aaa gat gca ggt ttt gat cat gta aga att ccc     144
Tyr Phe Lys Ile Val Lys Asp Ala Gly Phe Asp His Val Arg Ile Pro
        35                  40                  45 ata aag tgg agt gtt tat act caa aaa gaa gcc cca tat tct att gag     192
Ile Lys Trp Ser Val Tyr Thr Gln Lys Glu Ala Pro Tyr Ser Ile Glu
    50                  55                  60 aaa aga att ttt gac aga gtg gat cat tta ata gaa gaa gga ctt aaa     240
Lys Arg Ile Phe Asp Arg Val Asp His Leu Ile Glu Glu Gly Leu Lys
65                  70                  75                  80 aat aat ctc cat gtt att ata aac att cat cat tat gaa gag ata atg     288
Asn Asn Leu His Val Ile Ile Asn Ile His His Tyr Glu Glu Ile Met
                85                  90                  95 gag gat ccc tta ggg gaa aaa gaa aga ttt cta gct ata tgg aga cag     336
Glu Asp Pro Leu Gly Glu Lys Glu Arg Phe Leu Ala Ile Trp Arg Gln
            100                 105                 110 att tct gaa cac tac aag gat tac cct aat aat ctt tat ttt gaa ctt     384
Ile Ser Glu His Tyr Lys Asp Tyr Pro Asn Asn Leu Tyr Phe Glu Leu
        115                 120                 125 tta aat gag cct act caa aat ctg agt agt gaa tta tgg aat cag ttt     432
Leu Asn Glu Pro Thr Gln Asn Leu Ser Ser Glu Leu Trp Asn Gln Phe
    130                 135                 140 tta aaa gag gct att gaa gtt ata agg aga acg aat cct gaa agg aag     480
Leu Lys Glu Ala Ile Glu Val Ile Arg Arg Thr Asn Pro Glu Arg Lys
```

```
                     145                 150                 155                 160
att att gta gga cca gat aat tgg aat agt tta tat aat ctt gag aaa            528
Ile Ile Val Gly Pro Asp Asn Trp Asn Ser Leu Tyr Asn Leu Glu Lys
                165                 170                 175 ttg ata att cca gaa aat gat gag aat atc ata att act ttt cat tat            576
Leu Ile Ile Pro Glu Asn Asp Glu Asn Ile Ile Ile Thr Phe His Tyr
                180                 185                 190 tac aat cct ttc cct ttt act cat cag ggg gca ggg tgg gta aaa att            624
Tyr Asn Pro Phe Pro Phe Thr His Gln Gly Ala Gly Trp Val Lys Ile
            195                 200                 205 gat tta cct gta gga gta aaa tgg tta ggt act gag gaa gag aaa agg            672
Asp Leu Pro Val Gly Val Lys Trp Leu Gly Thr Glu Glu Glu Lys Arg
        210                 215                 220 gaa ata gaa aga gaa ctt gat atg gca gta agt tgg gca gaa gag cat            720
Glu Ile Glu Arg Glu Leu Asp Met Ala Val Ser Trp Ala Glu Glu His
225                 230                 235                 240 ggc aat ata ccc ctt tat atg ggg gag ttt gga gca tat tca aag gca            768
Gly Asn Ile Pro Leu Tyr Met Gly Glu Phe Gly Ala Tyr Ser Lys Ala
                245                 250                 255 gat atg gag tca agg gta agg tgg aca gat ttt gtg gca aga tct gca            816
Asp Met Glu Ser Arg Val Arg Trp Thr Asp Phe Val Ala Arg Ser Ala
                260                 265                 270 gaa aaa aga ggt att gct tgg tca tat tgg gaa ttt tat tct gga ttt            864
Glu Lys Arg Gly Ile Ala Trp Ser Tyr Trp Glu Phe Tyr Ser Gly Phe
            275                 280                 285 gga gtg ttt gat cct gag aaa aat gaa tgg aga acg cct ctt ctt agg            912
Gly Val Phe Asp Pro Glu Lys Asn Glu Trp Arg Thr Pro Leu Leu Arg
        290                 295                 300 gca tta ata cct gaa agg aat ata tga                                        939
Ala Leu Ile Pro Glu Arg Asn Ile
305                 310

<210> SEQ ID NO 2
<211> LENGTH: 312
<212> TYPE: PRT
<213> ORGANISM: Dictyoglomus turgidum

<400> SEQUENCE: 2

Met Asn Asn Leu Pro Ile Lys Arg Gly Ile Asn Phe Gly Asp Ala Leu
1               5                   10                  15

Glu Ala Pro Tyr Glu Gly Ala Trp Ser Gly Tyr Ile Ile Lys Asp Glu
            20                  25                  30

Tyr Phe Lys Ile Val Lys Asp Ala Gly Phe Asp His Val Arg Ile Pro
        35                  40                  45

Ile Lys Trp Ser Val Tyr Thr Gln Lys Glu Ala Pro Tyr Ser Ile Glu
    50                  55                  60

Lys Arg Ile Phe Asp Arg Val Asp His Leu Ile Glu Glu Gly Leu Lys
65                  70                  75                  80

Asn Asn Leu His Val Ile Asn Ile His His Tyr Glu Glu Ile Met
                85                  90                  95

Glu Asp Pro Leu Gly Glu Lys Glu Arg Phe Leu Ala Ile Trp Arg Gln
            100                 105                 110

Ile Ser Glu His Tyr Lys Asp Tyr Pro Asn Asn Leu Tyr Phe Glu Leu
        115                 120                 125

Leu Asn Glu Pro Thr Gln Asn Leu Ser Ser Glu Leu Trp Asn Gln Phe
    130                 135                 140

Leu Lys Glu Ala Ile Glu Val Ile Arg Arg Thr Asn Pro Glu Arg Lys
145                 150                 155                 160
```

```
Ile Ile Val Gly Pro Asp Asn Trp Asn Ser Leu Tyr Asn Leu Glu Lys
            165                 170                 175

Leu Ile Ile Pro Glu Asn Asp Glu Asn Ile Ile Thr Phe His Tyr
        180                 185                 190

Tyr Asn Pro Phe Pro Phe Thr His Gln Gly Ala Gly Trp Val Lys Ile
        195                 200                 205

Asp Leu Pro Val Gly Val Lys Trp Leu Gly Thr Glu Glu Lys Arg
    210                 215                 220

Glu Ile Glu Arg Glu Leu Asp Met Ala Val Ser Trp Ala Glu His
225                 230                 235                 240

Gly Asn Ile Pro Leu Tyr Met Gly Glu Phe Gly Ala Tyr Ser Lys Ala
            245                 250                 255

Asp Met Glu Ser Arg Val Arg Trp Thr Asp Phe Val Ala Arg Ser Ala
        260                 265                 270

Glu Lys Arg Gly Ile Ala Trp Ser Tyr Trp Glu Phe Tyr Ser Gly Phe
    275                 280                 285

Gly Val Phe Asp Pro Glu Lys Asn Glu Trp Arg Thr Pro Leu Leu Arg
290                 295                 300

Ala Leu Ile Pro Glu Arg Asn Ile
305                 310
```

<210> SEQ ID NO 3
<211> LENGTH: 2744
<212> TYPE: DNA
<213> ORGANISM: Artificial Sequence
<220> FEATURE:
<223> OTHER INFORMATION: Vector insert sequence
<220> FEATURE:
<221> NAME/KEY: misc_feature
<222> LOCATION: (2188)..(2188)
<223> OTHER INFORMATION: n is a, c, g, or t
<220> FEATURE:
<221> NAME/KEY: misc_feature
<222> LOCATION: (2728)..(2728)
<223> OTHER INFORMATION: n is a, c, g, or t
<220> FEATURE:
<221> NAME/KEY: misc_feature
<222> LOCATION: (2741)..(2742)
<223> OTHER INFORMATION: n is a, c, g, or t

<400> SEQUENCE: 3

```
ttaattttac ccatcagggt gcagattggg ttcaacctca acttcctgta ggagtaaaat      60
ggaccggttc tgaccaagag aaaaaagcta ttgagagaga acttgatttt actttggagt     120
gggcaaagag aaatggtaat gttctccttt acatggggga gtttggagca tattcaaagg     180
cagatatgga gtcaagggta aggtggacag attttgtagc aagatctgca gaaaaagag      240 gtattgcttg gtcatattgg gattttgcct cggcaggctt tggagtttat gatgggttaa     300
ataagatgtg gaggatcgaa ctcctcaaag cattgattcc tgaaacaaaa ataaaataga     360
taggagtggg gagagaatga acaatcttcc tattaagaga ggaattaatt ttggggatgc     420
tttagaagct ccttatgagg gggcttggag tggttatata attaaggatg aatattttaa     480
aattgttaaa gatgcaggtt ttgatcatgt aagaattccc ataaagtgga gtgtttatac     540
tcaaaaagaa gccccatatt ctattgagaa agaattttt gacagagtgg atcatttaat      600
agaagaagga cttaaaaata atctccatgt tattataaac attcatcatt atgaagagat     660
aatggaggat cccttagggg aaaaagaaag atttctagct atatggagac agatttctga     720
acactacaag gattacccta ataatcttta ttttgaactt ttaaatgagc ctactcaaaa     780
tctgagtagt gaattatgga atcagttttt aaaagaggct attgaagtta taaggagaac     840
```

```
gaatcctgaa aggaagatta ttgtaggacc agataattgg aatagtttat ataatcttga    900
gaaattgata attccagaaa atgatgagaa tatcataatt acttttcatt attacaatcc    960
tttccctttt actcatcagg gggcagggtg ggtaaaaatt gatttacctg taggagtaaa   1020
atggttaggt actgaggaag agaaaaggga aatagaaaga gaacttgata tggcagtaag   1080
ttgggcagaa gagcatggca atataccoct ttatatgggg gagtttggag catattcaaa   1140
ggcagatatg gagtcaaggg taaggtggac agattttgtg gcaagatctg cagaaaaaag   1200
aggtattgct tggtcatatt gggaatttta ttctggatt ggagtgtttg atcctgagaa   1260
aaatgaatgg agaacgcctc ttcttagggc attaatacct gaaaggaata tatgaactta   1320
ttttagatag gaggtatagt tttgaagata aaaaatgtta ttccgagatg aagggtttt    1380
aatctgacaa atatgtttct ttttcatctt gcgaaggatt ttgatgagga agattttaag   1440
tggattagtg agtgggtttt aactttgtt agaattcccc tttgttatag ctatggata    1500
gaagatgata atgtttacaa aataaaggaa gaaattttag agaaaataga taaagtggtg   1560
gcatggggc aaaagtacaa tattcatgtt tctttaaatt ttcacagagc acctggctat   1620
tgtgtaaaca atgaatttac agaaaaattt aatctctgga gggatgaatc tgctcttgat   1680
gccttttgct ttcattgggg tatttttgcg aaaagatata aagggtttc atctaagtat   1740
ttaagttttta atttggtaaa tgagcctttg catccttctc ctgaagtcat gacaagagag   1800
gatcataata gagtaattag gcgcacagta gaatatataa gaaatattga ttcagaaagg   1860
ctgatcatta tagatggtat ttcctatgga aattctcctc ttccagagct ttcagatctt   1920
aatgtagtcc aaagttgtag gggatatctt cctatgggc ttacccatta taaagcaaat   1980
tgggtggggg gagaaaattg gccagagccc aagtggccag gcgcctggca ttatggagaa   2040
atatgggata gggaaaaact tggaagacat tatgatgagt gggcaaaact aataggaatg   2100
ggagtaggag ttcattgtgg agaggcgggg gcatataagt ttacacctca taaggtagta   2160
atcgcatggc ttagagatct tcttgagntt ttaaaagaaa gggatatagg ttttgcactt   2220
tggaatttta agggaccttt tggtattctt gattctggta gatcagatgt ggagtatgag   2280
attgtatgac ataagcttga tagggagatg ttaaactttt gcagggtact aaggagactt   2340
tttgtagatc tctatttat agccatcttt tcctgatagc attattatta aaaagttttc   2400
gttttttgag aattgaatat cttccacaaa atagtcttct ttaagattga ttctttttg    2460
ctcattgttt tccctattta taatgaggat ttcccttgaa agagaagcga aattcttgct   2520
caaagcataa gccatataag tttgggaagg agatagagaa gaattagatc ctaagtaggt   2580
tgctcattaa ttcttttattt ttaatatcaa atatattat acttctgttt ccttctacta   2640
ttagaaggtt ctcaagagga ctaaattta catagcctga gattggaagt gtagaaattt   2700
catttaaact gaacagcttg gcgtaatnat ggtctaactg nnac               2744
```

<210> SEQ ID NO 4
<211> LENGTH: 335
<212> TYPE: PRT
<213> ORGANISM: Thermotoga sp. strain RQ2

<400> SEQUENCE: 4

```
Met Lys Asn Phe Leu Leu Phe Leu Leu Met Ile Leu Ile Met Gly Gly
1               5                   10                  15

Ile Val Met Gly Val Asp Pro Phe Glu Arg Asn Lys Ile Leu Gly Arg
            20                  25                  30

Gly Ile Asn Ile Gly Asn Ala Leu Glu Ala Pro Asn Glu Gly Asp Trp
        35                  40                  45
```

```
Gly Val Val Ile Lys Asp Glu Phe Phe Asp Ile Ile Lys Glu Ala Gly
         50                  55                  60

Phe Ser His Val Arg Ile Pro Ile Arg Trp Ser Thr His Ala Tyr Ala
 65                  70                  75                  80

Phe Pro Pro Tyr Lys Ile Met Asp Arg Phe Phe Lys Arg Val Asp Glu
                 85                  90                  95

Val Ile Asn Gly Ala Leu Lys Arg Gly Leu Ala Val Val Ile Asn Ile
            100                 105                 110

His His Tyr Glu Glu Leu Met Asn Asp Pro Glu Glu His Lys Glu Arg
        115                 120                 125

Phe Leu Ala Leu Trp Lys Gln Ile Ala Asp Arg Tyr Lys Asp Tyr Pro
130                 135                 140

Glu Thr Leu Phe Phe Glu Ile Leu Asn Glu Pro His Gly Asn Leu Thr
145                 150                 155                 160

Pro Glu Lys Trp Asn Glu Leu Leu Glu Glu Ala Leu Lys Val Ile Arg
                165                 170                 175

Ser Ile Asp Lys Asn His Thr Ile Ile Gly Thr Ala Glu Trp Gly
                180                 185                 190

Gly Ile Ser Ala Leu Glu Lys Leu Ser Val Pro Glu Trp Glu Lys Asn
            195                 200                 205

Ser Ile Val Thr Ile His Tyr Tyr Asn Pro Phe Glu Phe Thr His Gln
210                 215                 220

Gly Ala Glu Trp Val Glu Gly Ser Glu Lys Trp Leu Gly Arg Lys Trp
225                 230                 235                 240

Gly Ser Pro Asp Asp Gln Lys His Leu Ile Glu Glu Phe Asn Phe Ile
                245                 250                 255

Glu Glu Trp Ser Lys Lys Asn Lys Arg Pro Ile Tyr Ile Gly Glu Phe
                260                 265                 270

Gly Ala Tyr Arg Lys Ala Asp Leu Glu Ser Arg Ile Lys Trp Thr Ser
            275                 280                 285

Phe Val Val Arg Glu Met Glu Lys Arg Arg Trp Ser Trp Ala Tyr Trp
290                 295                 300

Glu Phe Cys Ser Gly Phe Gly Val Tyr Asp Thr Leu Arg Lys Thr Trp
305                 310                 315                 320

Asn Lys Asp Leu Leu Glu Ala Leu Ile Gly Gly Asp Ser Ile Glu
                325                 330                 335

<210> SEQ ID NO 5
<211> LENGTH: 20
<212> TYPE: PRT
<213> ORGANISM: Dictyoglomus turgidum

<400> SEQUENCE: 5

Met Asn Asn Leu Pro Ile Lys Arg Gly Ile Asn Phe Gly Asp Ala Leu
 1               5                  10                  15

Glu Ala Pro Tyr
            20

<210> SEQ ID NO 6
<211> LENGTH: 30
<212> TYPE: DNA
<213> ORGANISM: Artificial Sequence
<220> FEATURE:
<223> OTHER INFORMATION: PCR primer

<400> SEQUENCE: 6
aacaatctta ttaagagagg aattaatttt                                         30
```

```
<210> SEQ ID NO 7
<211> LENGTH: 30
<212> TYPE: DNA
<213> ORGANISM: Artificial Sequence
<220> FEATURE:
<223> OTHER INFORMATION: PCR primer

<400> SEQUENCE: 7
tcatatattc ctttcaggta ttaatgccct                                30
```

THERMOSTABLE CELLULASE AND METHODS OF USE

CROSS-REFERENCE TO RELATED APPLICATIONS

Priority is hereby claimed to provisional application Ser. No. 61/108,216, filed Oct. 24, 2008, the content of which is incorporated herein by reference.

FIELD OF THE INVENTION

The invention is directed to thermostable cellulases purified from *Dictyoglomus turgidum*, polynucleotides and vectors encoding the cellulases, hosts expressing the cellulases, compositions of matter including the cellulases, and methods of using the cellulases.

BACKGROUND

Cellulose-containing plant cell walls provide an abundant and renewable source of glucose, pentoses, and other small carbon compounds, many of which have significant commercial value. For example, glucose is particularly valuable as a feedstock for yeast in the production of bioethanol. Other commercially valuable byproducts of enzymatic conversion of cellulosic materials may be used in the manufacture of chemical products such as plastics, solvents, chemical intermediates, phenolics, adhesives, furfural, fatty acids, acetic acid, carbon black, paints, dyes, pigments, inks, and detergents; in the production of power; and in food and feed products. Accordingly, there has been substantial interest in developing improved techniques for microbial enzymatic processing of cellulosic materials.

Microbial cellulases represent an enormous range of proteins with widely varying specificities, cleavage patterns, and operating parameters. Among the cellulose-degrading enzymes, there are endo-acting cellulases that cleave at internal sites on the cellulose chain, exo-acting cellulases that cleave fragments from the ends of the cellulose chain, and β-glucosidases that hydrolyze soluble fragments to glucose. The diversity of cellulases is demonstrated by their presence in seven glycoside hydrolase families (Families 1, 5, 6, 7, 9, 10, and 48). Generally, cellulase-degrading enzymes produced by aerobic bacteria are soluble, while those produced by anaerobic bacteria are bound in large, multicomponent extracellular enzyme complexes called cellulosomes.

Thermophilic, cellulase-producing microbes have been isolated and identified. In particular, known cellulase-producing thermophiles capable of growing at 70° C. or higher include both aerobes (e.g., *Caldibacillus cellovorans*, *Rhodothermus marinus* and *Acidothermus cellulolyticus*) and anaerobes (e.g., *Anaerocellum thermophilum*, *Caldicellulosiruptor saccharolyticus*, *Clostridium thermocellum*, *Fervidobacterium islandicum*, *Spirochaeta thermophila*, *Thermotoga maritime* and *Pyrocccus furiosus*).

Despite the fact that several thermophilic microorganisms are known to produce cellulases, there remains no source of thermostable cellulase suitable for commercial use for most applications, including bioethanol production. The current commercially available products are mixtures of fungal cellulases that have effective temperature ranges of from 20° C. to 50° C. Much of the research on cellulases has focused on fungal cellulase systems, particularly the cellulytic system of *Trichoderma reesei*. This multi-component enzyme system has many benefits, including the ability to produce high yields of glucose from acid-treated cellulose. However, the cellulase enzymes from this organism are not stable for extended periods of time at high temperatures (greater than 60° C.). Thus, they must be used at temperatures below 40° C.

Some success has been reported in improving the thermostability of cellulase compositions by either site-directed mutagenesis or by cloning more thermostable endoglucanases into *T. reesei*. However, the improved *T. reesei* enzyme products remain unsuitable for use in starch liquefaction, and it is unlikely that the thermostability of all the components in the compositions could ever be increased sufficiently for the product to work under those conditions. An additional problem with *T. reesei*-derived enzyme products is that the cellulosic feedstock requires extensive pretreatment before being digested with the enzymes. To obtain adequate conversion, the cellulose must be pretreated with acid, high temperature steam, ammonia, or other extreme processing conditions to break down the crystal structure of the cellulose. While these pretreatments may be acceptable for use with cellulosic materials, these pretreatments are not practical within the processes currently used in the production of bioethanol, among other commercial applications.

SUMMARY

The invention is principally directed to a previously uncharacterized, soluble, thermostable cellulase purified from *Dictyoglomus turgidum* that exhibits both endo- and exoglucanase activities. In addition, the cellulase is stable over a broad temperature range, permitting its use in various industrial applications in which high temperatures preclude the use of non-thermostable cellulases.

Accordingly, in one aspect, the invention comprises a purified thermostable cellulase comprising an amino acid sequence having at least about 80% identity to SEQ. ID. NO: 2. The cellulase exhibits endoglucanase or exoglucanase activity, or may exhibit both activities. The cellulase is active in soluble form. In other aspects, the invention provides a polynucleotide construct which comprises a polynucleotide encoding the cellulase operably connected to a promoter. The construct may be inserted in an expression vector to drive expression of the cellulase in a heterologous host. Such vectors are encompassed in the invention. Also encompassed in the invention are recombinant host cells which include the polynucleotide construct or a vector comprising the polynucleotide construct.

In another aspect, the invention comprises a transgenic plant which includes a polynucleotide construct that encodes and expresses the thermostable cellulase described herein.

In yet another aspect, the invention comprises a composition of matter which includes the thermostable cellulase. Additional components of the composition may include one or more of an α-amylase, a glucoamylase, a xylanase, a β-xylosidase, and a β-glucosidase.

In still another aspect, the invention comprises a method of producing at least one cellulose byproduct by enzymatically digesting a cellulose-containing feedstock using the cellulase described herein. The method includes contacting a cellulosic material with the cellulase under conditions wherein the cellulase is active for a period of time sufficient to allow the cellulase to digest the celluose, thereby yielding a cellulose byproduct.

In a further aspect, the invention comprises a method of producing ethanol including the steps of contacting a source of cellulose with the cellulase described herein to produce cellobiose, contacting the cellobiose with a β-glucosidase to produce glucose, and then fermenting the glucose to produce ethanol.

Any embodiment of any method or composition of the invention may be used with any other method or composition of the invention.

All combinations of method or process steps as used herein can be performed in any order, unless otherwise specified or clearly implied to the contrary by the context in which the referenced combination is made.

As used in this specification and the appended claims, the singular forms "a," "an," and "the" include plural referents unless the content clearly dictates otherwise. Thus, for example, reference to a composition containing "a polynucleotide" includes a mixture of two or more polynucleotides. The term "or" is generally employed in its sense including "and/or" unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All publications, patents and patent applications are herein expressly incorporated by reference to the same extent as if each individual publication or patent application was specifically and individually indicated by reference. In case of conflict between the present disclosure and the incorporated patents, publications, and references, the present disclosure should control.

The methods, compounds, and compositions of the present invention can comprise, consist of, or consist essentially of the essential elements and limitations described herein, as well as any additional or optional steps, ingredients, components, or limitations described herein or otherwise useful in biochemistry, enzymology and/or genetic engineering.

BRIEF DESCRIPTION OF THE FIGURES

FIG. 1 is a an amino acid sequence alignment of DtuC2, a thermostable cellulase purified from *Dictyoglomus turgidum* (SEQ. ID. NO: 2), with a glycoside hydrolase of *Thermotoga* sp. RQ2 (SEQ. ID. NO: 4).

DETAILED DESCRIPTION

Figure 2:
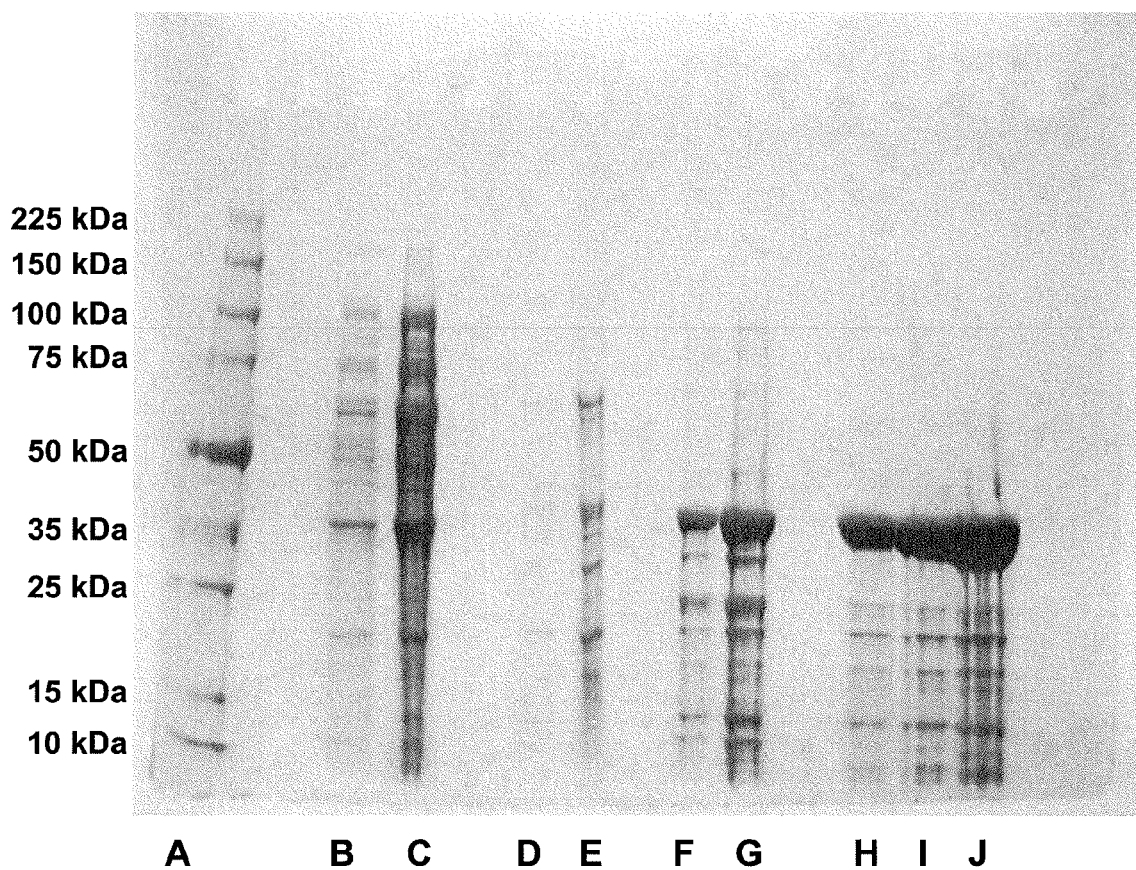
FIG. 2 is a photograph of an SDS-PAGE gel showing the separation of proteins recovered during the expression and isolation of the DtuC2 thermostable cellulase.

A previously uncharacterized enzyme was purified from *Dictyoglomus turgidum* and found to exhibit cellulase activity. Accordingly, in one embodiment, the invention comprises a purified thermostable cellulase comprising the amino acid sequence of SEQ. ID. NO: 2, or a purified thermostable cellulase having an amino acid sequence at least 60% homologous to the sequence shown in SEQ. ID. NO: 2. A cellulase consisting of the exact sequence of 312 amino acids shown in SEQ. ID. NO: 2 is referred to herein as "DtuC2." This cellulase has a predicted molecular weight of about 37 kDa.

As used herein, the term "cellulase" refers to an enzyme that catalyzes the hydrolysis of cellulose.

The purified cellulases of the invention are thermostable. As used herein, "thermostable" as applied to cellulases means that they retain their activity at temperatures greater than about 40° C. The purified cellulases of the invention also exhibit activity in soluble form, i.e., they exhibit activity independent of association with a cellulosome or related proteins such as scaffoldins. The cellulases described herein are useful in any research or commercial context where cellulases are conventionally utilized.

As used herein, the term "purified" refers to material that is substantially or essentially free from components which normally accompany it in its native state. Purity of a polypeptide species is typically determined using analytical chemistry techniques such as sodium dodecyl sulfate polyacrylamide gel electrophoresis (SDS-PAGE) or high performance liquid chromatography (HPLC). A polypeptide that is the predominant species present in a preparation is considered substantially purified. The term "substantially purified" denotes that a preparation containing the polypeptide may give rise to essentially one band in an electrophoretic gel. Preferably, cellulases of the invention are at least about 85% pure, more suitably at least about 95% pure, and most suitably at least about 99% pure as determined by band density in an electrophoretic gel.

Purified cellulases of the invention preferably have an amino acid sequence having at least about 80% identity, more preferably at least about 85% identity, more preferably at least about 90% identity, more preferably at least about 95% identity, and most preferably at least about 98% or 99% identity, to the amino acid sequence provided in SEQ. ID. NO: 2. Percent identity may be determined using the algorithm of Altschul et al., *Nucleic Acids Res.* 25:3389-3402 (1997) Such algorithm is incorporated into the BLASTP program, which may be used to obtain amino acid sequences homologous to a reference polypeptide, as is known in the art. As will be appreciated, the invention also encompasses cellulases having amino acid sequences including conservative amino acid substitutions. As a general rule, amino acid substitutions with BLOSUM62 scores≧0 are considered conservative substitutions. See, for example, Ng & Henikoff (May 2001) *Genome Research* 11(5):863-874. Such substitutions are well known in the art.

DtuC2 has some amino acid homology to cellulases and glycosidases. BLASTP searches revealed that DtuC2 is homologous to a Family 5 glycoside hydrolase of *Thermotoga* sp. RQ2 (SEQ. ID. NO: 4). The *Thermotoga* sp. had 52% amino acid identity and 68% amino acid similarity over 311 amino acids relative to DtuC2. See FIG. 1.

A BLASTP search for conserved domains demonstrated that DtuC2 has similarity to cellulases in the region from amino acid 14-287 of the protein and to glycosyl hydrolases in the region from amino acid 124-133. The homology information suggested that DtuC2 was a novel protein that would have both cellulase and β-glucanase activity.

The purified cellulases of the invention exhibit endoglucanase activity, exoglucanase activity, or combinations thereof. Endoglucanase activities exhibited by cellulases of the invention include β-glucanase, cellulase, and/or endoxylanase activity. Exoglucanase activities exhibited by cellulases of the invention suitably includes exocellulase activity. Exemplary definitions of each of the above-mentioned activities include the ability to degrade specific substrates as shown in the Examples. As will be appreciated, the type of activity of a cellulase may be determined by any method known in the art. For example, endo- or exoglucanase activity may be determined by incubating the enzyme with commercially available fluorescent test substrates and detecting fluorescence using automated methods or direct visualization. Alternatively, enzyme activity may be detected by measuring reducing sugars using, for example, a commercially available chromogenic assay. See also Green et al. (1989) *Anal. Biochem.* 182:

197-199 for a description of a suitable assay in microtiter plate format. As another alternative, oligomeric sugars can be hydrolyzed to monomeric sugars, which in turn may be measured by high performance liquid chromatography (HPLC).

The invention also provides DNA constructs useful in preparing the cellulases of the invention. The DNA constructs include at least one polynucleotide encoding the polypeptides described herein, operably connected to a promoter. As used herein, a promoter includes an expression control sequence near the start site of transcription. A promoter may optionally include distal enhancer or repressor elements which may be non-contiguous with the start site of transcription. The promoter may be a "heterologous" promoter, i.e., a promoter not natively associated with the coding sequence. The promoter may be constitutive or inducible. A "constitutive" promoter is a promoter that is active under most environmental and developmental conditions. An "inducible" promoter is a promoter that is under environmental or developmental regulation. The term "operably connected" refers to a functional linkage between a regulatory sequence (such as a promoter) and a second nucleic acid sequence, wherein the regulatory sequence directs transcription of the nucleic acid corresponding to the second sequence. A nucleotide coding sequence for DtuC2 is shown in SEQ. ID. NO: 1; the encoded amino acid sequence is also depicted in SEQ. ID. NO: 1. The amino acid sequence of the expressed cellulase is shown in SEQ. ID. NO: 2.

The polynucleotide constructs may suitably be introduced into host cells, such as *E. coli* or other suitable hosts known in the art, for producing cellulases of the invention. Such host cells are termed herein as "recombinant host cells." Methods of introducing polynucleotide constructs into host cells are well known in the art, as are suitable expression systems, many of which are commercially available. For example, Promega (Madison, Wis.), Applied Biosystems (Foster City, Calif.), and New England BioLabs (Ipswich, Mass.), among many others, sell expression system kits. The polynucleotide constructs may be introduced into the host cells using vectors that are maintained in the host cell cytoplasm or those that are integrated into the genome of the host cell.

In some embodiments, the host cell is a plant cell. The recombinant plant cell may be used to produce a transgenic plant that expresses a cellulase of the invention. As will be appreciated, expression of a cellulase by a plant containing cellulosic material can eliminate processing steps in methods of producing cellulose byproducts from the transgenic plant. Suitably, the cellulase may be released upon mechanical or chemical disruption of the transgenic plant cell in a reaction mixture and will become available to hydrolyze cellulose to cellobiose without the need for first expressing and purifying the enzyme in, e.g., a bacterial expression system. The growth properties of the transgenic plant will not be adversely affected by the expression of the cellulase. This can be accomplished by targeting the transgene to particular cells or tissues using cell- or tissue-specific promoters, for example, a promoter for a seed storage protein. The polynucleotide construct may be expressed in seeds, as described in U.S. Pat. No. 7,033,627, or in chloroplasts, as described in U.S. Pat. No. 6,680,426. These patents are incorporated herein by reference.

In some embodiments, the cellulase of the invention may be included in a composition of matter. Compositions including the cellulase may optionally include further enzymes useful in processing plant material, such as a β-glucosidase, a xylanase, a β-xylosidase, an α-amylase and a glucoamylase.

A "β-glucosidase" is an enzyme that cleaves the β bonds linking two glucose or glucose-substituted molecules. Suitable β-glucosidases include but are not limited to any one or combination of enzymes classified under Enzyme Commission (EC) numbers 3.2.1.21, 3.2.1.39, 3.2.1.58, 3.2.1.71, 3.2.1.74, 3.2.1.75, 3.2.1.86, 3.2.117, 3.2.1.118, 3.2.1.119, 3.2.1.125, 3.2.1.126, and 3.2.1.161.

A "xylanase" is an enzyme that degrades the polysaccharide xylan, a component of the cell walls of plants and some algae. Suitable xylanases include but are not limited to any one or combination of enzymes classified under EC numbers 3.2.1.8, 3.2.1.32, 3.2.1.136, and 3.2.1.156.

A "β-xylosidase" is an enzyme that cleaves the β bonds in the polysaccharide xylan. Suitable β-xylosidases include but are not limited to any one or combination of enzymes classified under EC numbers 3.2.1.32, 3.2.1.37, and 3.2.1.72.

An α-amylase is a glycoside hydrolase that performs endohydrolysis of α(1→4) glycosidic bonds in oligosaccharides and polysaccharides. Suitable α-amylases include but are not limited to enzymes classified under EC number 3.2.1.1.

A "glucoamylase" is a glycoside hydrolase that cleaves terminal α(1→4) glycosidic linkages and terminal α(1→6) glycosidic linkages in oligosaccharides and polysaccharides. Suitable glycoamylases include but are not limited to any one or a combination of enzymes classified under EC numbers 3.2.1.3 and 3.2.1.20.

Other amylases that may be combined with the cellulases of the invention include but are not limited to any one or combination of enzymes classified under EC numbers 3.2.1.2, 3.2.1.60, 3.2.1.68, 3.2.1.98, 3.2.1.116, 3.2.1.133, and 2.4.1.161.

A cellulase of the invention may be combined with any one or combination of the above-listed enzymes.

Optionally, any or all of the enzymes used in such compositions may be thermostable. For example, thermostable β-glucosidases are well known in the art and are readily obtainable. See, e.g., Zverlow et al., *Microbiology*, 143: 3537-3542 (1997); Kengen et al., *Eur. J. Biochem.* 213:305-312; Wang et al., *J. Bacteriol.* 185(4): 4248-55 (2003); Wright et al., *Appl. and Env. Microbiol.*, 58(11): 3455-3465 (1992); and Breves et al., *Appl. and Env. Microbiol.*, 63(10): 3902-10 (1997), the disclosures of which are incorporated herein by reference.

The invention also provides a method of producing a cellulose byproduct. The method includes a step of contacting a cellulosic material with a cellulase of the invention to produce a first byproduct. Preferably the first byproduct is cellobiose. The method optionally comprises a step of contacting the cellobiose with a β-glucosidase to produce a soluble sugar. Suitably, the β-glucosidase is thermostable. Preferably, the soluble sugar produced by action of the β-glucosidase is glucose. In a further optional step, the glucose is fermented to produce a second byproduct. Preferably, the second byproduct is ethanol, lactic acid or acetone. Suitable organisms used for fermenting ethanol, lactic acid, or acetone from glucose are well-known in the art. Suitable reaction conditions for the steps of the method may be determined by skilled artisans. In some embodiments, the step of contacting the cellulosic material with a cellulase of the invention is carried out at a temperature of from about 40° C. to about 90° C. More suitably, the temperature is from about 60° C. to about 85° C. Most suitably, the temperature is from about 70° C. to about 80° C. In some embodiments, the step of contacting the cellulosic material with the cellulase of the invention is carried out at a pH of from about 4.0 to about 7.0. More suitably, the pH is from about 5.0 to about 7.0. Most suitably, the pH is from about 5.5 to about 6.5.

An additional embodiment of the invention provides a method of producing ethanol. The first step in the method is to contact a source of cellulose with the cellulase of the invention under temperature and pH conditions sufficient to produce cellobiose. Preferably, the conditions include a temperature of from about 40° C. to about 90° C., more preferably from about 60° C. to about 85° C., and most preferably 70° C. to about 80° C. The preferred pH of the reaction is from about 4.0 to about 7.0, more preferably from about 5.0 to about 7.0, and most preferably from about 5.5 to about 6.5. The duration of incubation will vary depending upon the amount of cellulose in the source, the amount of cellulase present, and other factors, and may be determined by the skilled artisan by routine optimization. In a second step, the cellobiose is contacted with a β-glucosidase under conditions sufficient to produce glucose. A third step includes fermenting the glucose under conditions sufficient to produce ethanol. Suitable conditions for the second and third steps may be determined by the skilled artisan.

Preferably, in the methods of producing ethanol, the source of cellulose is a plant material. The plant material may be from any source, without limitation, including wood, corn, sorghum (milo), giant cane, switchgrass, miscantus, rice, barley, wheat, and the like. The plant material may also be derived from paper, textiles, municipal waste, etc.

EXAMPLES

The following examples are provided to assist in a further understanding of the invention. The particular materials and conditions employed are intended to be further illustrative of the invention and are not limiting on the scope of the appended claims.

Example 1

Materials and Methods

*Dictyoglomus turgidum* strain 6724$^T$ bacterial cell concentrate was a kind gift of Dr. Frank T. Robb, Center of Marine Biotechnology, University of Maryland Biotechnology Institute. *Dictyoglomus turgidum* strain 6724$^T$ is deposited at Deutsche Sammlung von Mikroorganismen and Zellkulturen GmbH, "DSMZ"—The German Resource Centre for Biological Material, Inhoffenstraβe 7 B 38124 Braunschweig, Germany, under accession no. 6724. The deposit was made in 1988 and is available for purchase by the public. See Svetlichny & Svetlichnaya (1988), "*Dictyoglomus turgidus* sp. nov., a new extremely thermophilic eubacterium isolated from hot springs of the Uzon volcano caldera," *Mikrobiologiya* 57: 435-441. The cell concentrate was lysed using a combination of SDS and proteinase K, and genomic DNA was purified using phenol/chloroform extraction. The genomic DNA was precipitated, treated with RNase to remove residual contaminating RNA, and fragmented by hydrodynamic shearing ("HYDROSHEAR"-brand apparatus, GeneMachines, San Carlos, Calif.) to generate fragments of 2-4 kb. The fragments were purified on an agarose gel, end-repaired, and ligated into the "pEZSEQ"-brand lac promoter vector (Lucigen, Middleton, Wis.).

Enzyme activity was measured using the "Reducing Sugar Assay by Modified Somogyi Method" (see below). Substrate specificity for endo-activities was measured using azurine cross-linked-labeled and azo-labeled insoluble substrates (Megazyme International Ireland, Ltd., Wicklow, Ireland). Substrate specificity for exo-activity was determined using 4-methylumbelliferyl-β-D-cellobioside, 4-methylumbelliferyl-β-D-xylopyranoside, 4-methyl umbelliferyl-β-D-glucopyranoside and 5-bromo-6-chloro-3-indolyl-β-D-glucopyranoside (Magenta-β-D-glucopyranoside).

Reducing Sugar Assay by Modified Somogyi Method:
Reagents:

Reagent A: Dissolve 25.0 g anhydrous sodium carbonate, 25.0 g sodium potassium tartrate and 200 g anhydrous sodium sulfate in 600 ml of deionized water and adjust the volume to 1000 ml.

Reagent B: Dissolve 30.0 g of copper sulfate in 200 ml of deionized water containing 4 drops of concentrated sulfuric acid.

Reagent C: Dissolve 50.0 g of ammonium molybdate in 900 ml of deionized water. Carefully add 42 ml of concentrated sulfuric acid to the solution. Dissolve 6.00 g of sodium arsenate heptahydrate in 50 ml of deionized water and add to the solution above. Adjust volume to 1000 ml.

Reagent D: Add 1.00 ml of Reagent B to 25.0 ml of Reagent A.

Reagent E: Dilute Reagent C 5× with deionized water before use.

Substrate: 1% β-Glucan. Dissolve 1.00 g of β-glucan, from barley, low viscosity (Megazyme) in 40 ml of deionized water by heating to boiling with stirring. Cool to room temperature, add 2.50 ml of 1 M acetic acid-sodium acetate buffer, pH 5.8, and adjust volume to 50.0 ml. Prepare fresh daily.

Reducing Sugar Assay: P 1. Dispense 200 µl of substrate into 1.5 ml "BOILPROOF"-brand tubes (Axygen Scientific, Inc., Union City, Calif.). Include at least two blanks and two tubes per sample.

2. Incubate substrate tubes for 5 minutes at 70° C. in heat block.

3. Add 5 µl enzyme samples into tubes. Add 5 µl of deionized water to blanks.

4. Incubate for 10 minutes.

5. Remove tubes from heat block. Add 200 µl of Reagent D.

6. Vortex briefly to mix.

7. Place tubes in 95° C. heat block.

8. Incubate at 95° C. for 20 minutes.

9. Remove tubes and vortex briefly to mix. (Tubes should have an orange hue if the enzymes have broken down the substrate.)

10. Let the tubes sit at room temperature (~25° C.) for 5 minutes.

11. Add 600 µl of Reagent E.

12. Vortex or invert gently to mix.

13. Incubate at room temperature for 15 minutes.

14. If needed, centrifuge for 1-2 minutes at 13K to clarify.

15. Place 200 µl of each tube content into individual wells on a 96-well plate or into microcuvette.

16. Read absorbance (ABS) at 590 nm. If the absorbance values are outside the linear range of the standard curve, repeat at a higher dilution of enzyme. If using a plate reader with discrete filters, adequate results can be obtained by using a 630 nm filter for samples and standard curve.

17. Prepare a standard curve for xylose. Prepare 0.1 to 0.5 mM xylose standard solutions from a stock 1 M xylose solution. Pipette 200 µl of each standard and a blank sample containing deionized water into "BOILPROOF"-brand tubes (Axygen Scientific, Inc). Beginning at step 5, carry standards through procedure. Prepare a standard curve of A vs. micromoles xylose and determine $A_x$ the micromolar absorbance coefficient for your instrument.

Activity: 1.0 unit of enzyme activity generates 1 micromole of reducing sugar per minute under the assay conditions.

Calculations: $((\text{ABS of Sample} - \text{ABS Blank})/A_x) \times \frac{1}{10} \times 0.0005 = \text{units/ml}.$

Example 2

Identification of DtuC2

To identify cellulases, the *D. turgidum* library was transformed into electro-competent *E. coli* cells (Lucigen, Madison, Wis.) and screened on plates containing 30 µg/ml kanamycin and 100 µg/ml 4-methylumbelliferyl-β-D-cellobioside (MUC). Positive (blue-fluorescing) cells were picked, restreaked, and grown overnight at 37° C. in Terrific Broth (Difco, a wholly owned subsidiary of BD, Franklin Lakes, N.J.) containing 0.4% glycerol and 30 µg/ml kanamycin. The cultures were collected by centrifugation and lysed using "CELLYTIC IIB"-brand reagent (Sigma-Aldrich, St. Louis, Mo.). The lysates were assayed at 70° C. in 0.500 ml of 50 mM acetate buffer, pH 5.8 containing 0.2% AZCL-HE-Cellulose (Megazyme) for cellulase activity and in 0.500 ml of 50 mM acetate buffer, pH 5.8 containing 0.2% AZCL-Arabinoxylan (Megazyme) for hemicellulase activity. The lysate of one MUC-positive culture, designated DtuC2, was active on AZCL-HE-Cellulose but not on AZCL-Arabinoxylan, indicating that DtuC2 expressed a cellulase.

Example 3

Purification of DtuC2

*E. coli* cells containing the DtuC2 gene were grown overnight at 37° C. in 2000 ml of Terrific Broth (Difco) containing 0.4% glycerol and 30 µg/ml kanamycin. Cells (20.3 g) were resuspended in 1000 ml of 50 mM Tris-HCl, pH 8.0, and lysed by sonication. The lysate was clarified by centrifugation and *E. coli* proteins were precipitated by heat treatment at 80° C. for 15 minutes. The heat-treated lysate was clarified by centrifugation. The clarified material (90 ml) was diluted with an equal volume of 4 M $(NH_4)_2SO_4$ and then was applied to a 30 ml "OCTYL SEPHAROSE"-brand Fast Flow column (GE Healthcare, Waukesha, Wis.) equilibrated with 2 M $(NH_4)_2SO_4$. The column was washed with 120 ml of 2 M $(NH_4)_2SO_4$ in 100 mM Tris-HCl, pH 7.5, and eluted sequentially with 200 ml total gradients of a) 2 M $(NH_4)_2SO_4$ in 100 mM Tris-HCl, pH 7.5 to 100 mM Tris-HCl, pH 7.5 and b) 0% to 60% propylene glycol in 100 mM Tris-HCl, pH 7.5. Active fractions were pooled, diluted 1:1 with deionized water, and applied to a 15 ml "Q SEPHAROSE"-brand Fast Flow column (GE Healthcare) equilibrated with 50 mM Tris-HCl, pH 8.0. The column was washed with 20 ml of 50 mM Tris-HCl, pH 8.0, and the enzyme was eluted with a 100 ml gradient of 0 to 1000 mM NaCl in 50 mM Tris-HCl, pH 8.0. Active fractions were pooled and concentrated to 2.0 ml. The concentrate (0.8 ml aliquots) was diluted with 0.2 ml of 80% glycerol and applied to a 150 ml "SEPHACRYL"-brand S-100 High Resolution column (GE Healthcare) equilibrated with 50 mM Tris-HCl, pH 8.0. Active fractions were pooled and concentrated to 1.0 ml for characterization studies.

SDS denaturing gel electrophoresis was used to verify the purity and size of the cellulase. Electrophoresis was performed on a 4-20% gradient acrylamide gel. The results, shown in FIG. 2, show an approximately 37 kDa band in all fractions.

Example 3

Cloning of DtuC2

The DNA fragment containing the DtuC2 gene was sequenced; the nucleotide sequence is shown in SEQ. ID. NO: 3. Electronic translation of the DNA sequence did not yield an open reading frame of the correct size beginning with methionine. To determine the open reading frame, the N-terminal sequence of the purified protein was determined. N-terminal sequencing of a sample of the purified DtuC2 in Example 3 was performed by Commonwealth Biotechnologies, Inc., Richmond, Va. The sequence obtained was: MNNLPIKRGINFGDALEAPY (SEQ. ID. NO: 5).

Using 50 nanograms of template plasmid DNA, the cellulase gene was amplified using the following expression primers:

```
DTUC2 Forward:
5'-AACAATCTTATTAAGAGAGGAATTAATTT    (SEQ. ID. NO: 6)
T-3'.

DTUC2 Reverse:
5'-TCATATATTCCTTTCAGGTATTAATGCCC    (SEQ. ID. NO: 7)
T-3'.
```

The amplified PCR product was cloned into the ET28a vector (Novagen, a wholly owned subsidiary of Merck KGaA, Darmstadt, Germany). The ligated product was then transformed into BL21(DE3) competent cells (Lucigen) and the transformed clones were selected on plates containing kanamycin and 4-methylumbelliferyl-β-D-cellobioside. Eight transformants were picked, grown in 50 ml cultures, and induced with 1 mM isopropyl β-D-1-thiogalactopyranoside (IPTG). Lysates of the cultures were prepared and the expressed enzymes were shown to be identical in size and properties to the original purified sample of DtuC2.

Example 5

Characterization of DtuC2

Figure 3:
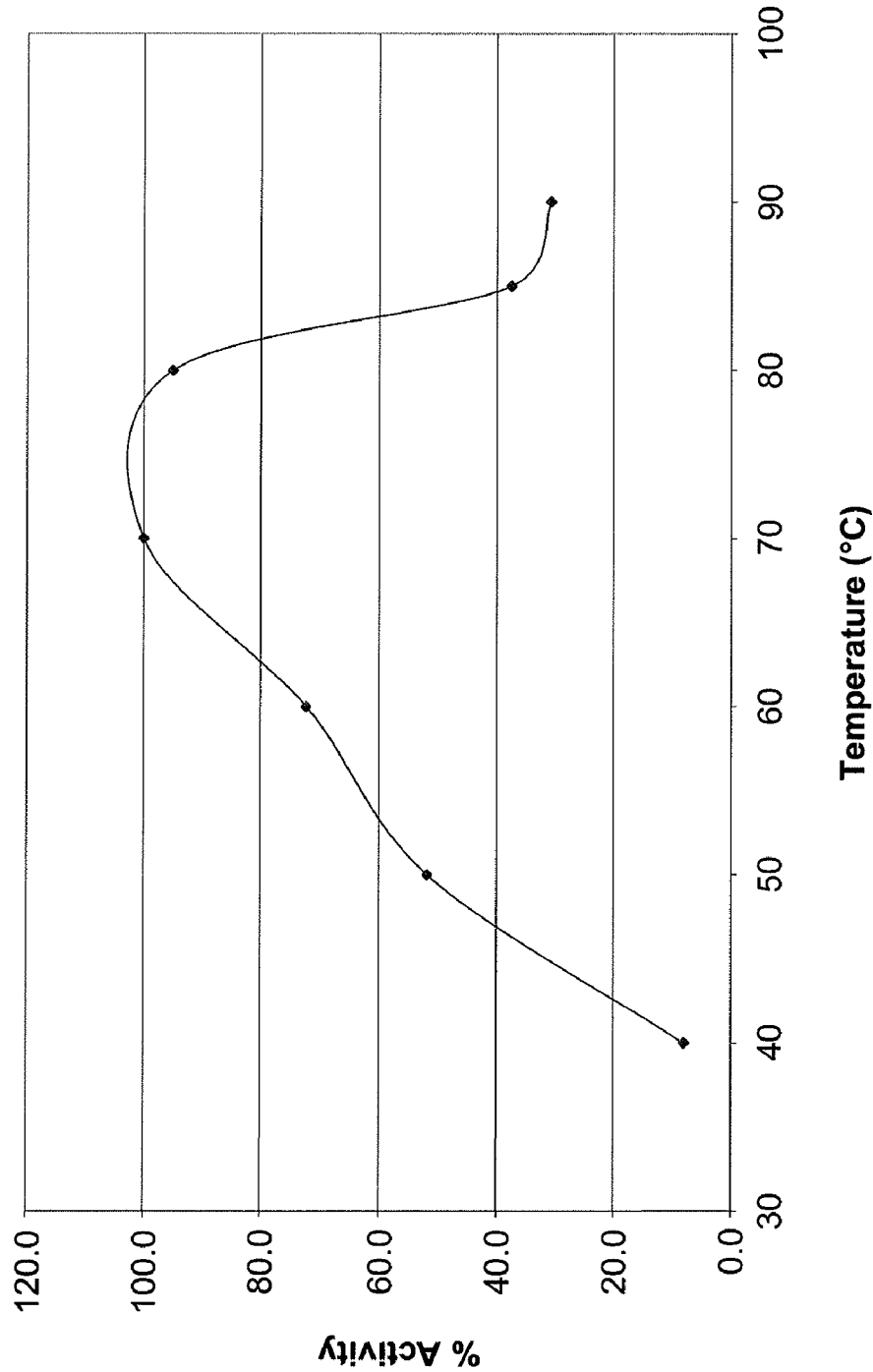
FIG. 3 is a graph of the relative activity of the DtuC2 thermostable cellulase as a function of temperature.

Temperature and pH optima: The temperature optimum of DtuC2 was determined using the Reducing Sugar Assay by Modified Somogyi Method as described earlier. The temperature curve is shown in FIG. 3. DtuC2 had a temperature optimum between 70° C. and 80° C. The activity of the enzyme dropped to approximately 30% of this maximum value at 90° C.

The pH optimum of DtuC2 was determined in 0.50 ml of 50 mM acetate buffer, containing 0.2% AZCL-HE-cellulose and 0.5 units of enzyme. Assays were performed at 1000 rpm, for 30 minutes in a "THERMOMIXER R"-brand dry block heating and cooling shaker (Eppendorf, Hamburg, Germany). Tubes were clarified by centrifugation and absorbance values determined using an "$EL_x800$"-brand plate reader (BioTek Instruments, Inc., Winooski, Vt.). DtuC2 exhibited activity over the pH range of 4.0 to 6.8, with maximum activity between pH 5.6 and 6.8.

Cellulase specific activity: The specific activity of DtuC2 was determined using the Reducing Sugar Assay by Modified Somogyi Method. A value of 226 u/mg was obtained.

Endoglucanase specificity: The endoglucanase specificity of DtuC2 was determined in 0.50 ml of 50 mM acetate buffer, pH 5.8, containing 0.2% insoluble substrate (as listed below in Table 1) and 1.0 µg of enzyme protein. Assays were performed at 70° C., 1000 rpm, for 20 minutes in a "THERMOMIXER R"-brand dry block heating and cooling shaker (Eppendorf). Tubes were clarified by centrifugation and absorbance values determined using an "$EL_x800$"-brand plate reader (BioTek Instruments, Inc.).

TABLE 1

Endoglucanase Activity of DtuC2

| Enzyme Activity | Substrate | Relative Activity |
|---|---|---|
| endocellulase | AZCL-HE-Cellulose (Megazyme) | 100% |
| β-glucanase | AZCL-β-glucan (Megazyme) | 55% |
| endoarabinoxylanase | AZCL-arabinoxylan (Megazyme) | 4% |
| galactaomannanase | AZCL-galactaomannan (Megazyme) | 4% |
| Endoxylanase | AZCL-xylan (Megazyme) | <1% |

DtuC2 demonstrated endocellulase activity when assayed using the Reducing Sugar Assay with cellulose powder (Sigma Chemical, St. Louis Mo.), soy flake (CHS, Mankato, Minn.), or AFEX-treated corn stover (Bruce Dale, Michigan State University East Lansing, Mich.) as substrate.

Exoglucanase specificity. The exoglucanase specificity of DtuC2 was determined by spotting enzyme directly on agar plates containing 10 mM substrate. Plates were incubated in a 70° C. incubator for 60 minutes; after incubation, the plates were examined using a hand-held UV lamp and compared to negative and positive controls.

TABLE 2

Exoglucanase Activity of DtuC2

| Enzyme Activity | Substrate | Relative Activity |
|---|---|---|
| exocellulase | 4-methylumbelliferyl-β-D-cellobioside | Strong Positive |
|  | 4-methylumbelliferyl-β-D-lactoside | Strong Positive |
| β-xylosidase | 4-methylumbelliferyl-β-D-xylopyranoside | Negative |
| β-glucosidase | 4-methylumbelliferyl-β-D-glucopyranoside | Positive |

As shown in Table 2, DtuC2 displayed strong exocellulase activity.

It is understood that the invention is not confined to the particular construction and arrangement of parts herein illustrated and described, but embraces such modified forms thereof as come within the scope of the following claims.

---

What is claimed is:

1. A purified thermostable cellulase comprising an amino acid sequence having at least about 90% identity to SEQ. ID. NO: 2.

2. The cellulase of claim 1, wherein the cellulase is active in soluble form.

3. A purified thermostable cellulase comprising an amino acid sequence having at least about 95% identity to SEQ. ID. NO: 2.

4. The cellulase of claim 3, comprising the amino acid sequence shown in SEQ. ID. NO: 2.

5. The cellulase of claim 1, wherein the cellulase exhibits β-glucanase, cellulase, or endoxylanase activity, or combinations thereof.

6. The cellulase of claim 1, wherein the cellulase exhibits exocellulase activity.

7. A polynucleotide construct comprising a polynucleotide encoding an amino acid sequence having at least about 90% identity to SEQ. ID. NO: 2, and a promoter operably connected thereto.

8. The polynucleotide construct of claim 7, wherein the promoter is a heterologous promoter.

9. A recombinant host cell comprising a polynucleotide construct comprising a polynucleotide encoding an amino acid sequence having at least about 90% identity to SEQ. ID. NO: 2, and a promoter operably connected thereto.

10. A recombinant plant cell comprising a polynucleotide construct comprising a polynucleotide encoding an amino acid sequence having at least about 90% identity to SEQ. ID. NO: 2, and a promoter operably connected thereto.

11. A transgenic plant comprising a recombinant plant cell comprising a polynucleotide construct comprising a polynucleotide encoding an amino acid sequence having at least about 90% identity to SEQ. ID. NO: 2, and a promoter operably connected thereto.

12. A composition of matter comprising the cellulase of claim 1.

13. The composition of claim 12, further comprising a β-glucosidase.

14. The composition of claim 12, further comprising an amylase.

15. The composition of claim 14, wherein the amylase comprises an α-amylase and a glucoamylase.

16. The composition of claim 12, further comprising a xylanase and β-xylosidase.

17. A method of producing at least one cellulose byproduct comprising contacting a cellulosic material with the cellulase of claim 1.

18. The method of claim 17, wherein a first byproduct is cellobiose.

19. The method of claim 18, further comprising contacting the cellobiose with a β-glucosidase to produce a soluble sugar.

20. The method of claim 19, wherein the β-glucosidase is thermostable.

21. The method of claim 19, wherein the soluble sugar is glucose.

22. The method of claim 21, further comprising fermenting the glucose to produce a second byproduct.

23. The method of claim 22, wherein the second byproduct is ethanol, lactic acid, or acetone.

24. The method of claim 17, wherein the method comprises contacting the cellulosic material with the cellulase at a temperature of from about 40° C. to about 90° C.

25. The method of claim 17, wherein the method comprises contacting the cellulosic material with the cellulase at a pH of from about 4.0 to about 7.0.

26. A method of producing ethanol comprising:
  a) contacting a source of cellulose with the cellulase of claim 1 to produce cellobiose;
  b) contacting the cellobiose with a β-glucosidase to produce glucose; and
  c) fermenting the glucose to produce ethanol.

27. The method of claim 26, wherein the source of cellulose is a plant material.

28. The method of claim 27, wherein the plant material is selected from the group consisting of wood, corn, sorghum (milo), giant cane, switchgrass, miscantus, rice, barley, and wheat.

29. The method of claim 28, wherein the source of cellulose is a paper or a textile.

30. The method of claim 26, wherein step (a) is performed at a temperature of from about 40° C. to about 90° C.

31. The method of claim 26, wherein step (a) is performed at a pH of from about 4.0 to about 7.0.

* * * * *